(12) United States Patent
Kawamura

(10) Patent No.: US 6,579,261 B1
(45) Date of Patent: Jun. 17, 2003

(54) DOUBLE LUMEN-TYPE CATHETER

(75) Inventor: Akira Kawamura, Tokyo Matropolis (JP)

(73) Assignee: Adam Spence Corporation, Wall, NJ (US)

( * ) Notice: Subject to any disclaimer, the term of this patent is extended or adjusted under 35 U.S.C. 154(b) by 112 days.

(21) Appl. No.: 09/608,609

(22) Filed: Jun. 30, 2000

Related U.S. Application Data

(60) Provisional application No. 60/144,247, filed on Jun. 19, 1999.

(51) Int. Cl.[7] ............................................. A61M 29/00
(52) U.S. Cl. ....................... 604/105; 604/104; 604/107; 604/537
(58) Field of Search ............................... 604/30, 96.01, 604/104, 105, 106, 107, 109, 167.06, 264, 284, 523, 537, 164

(56) References Cited

U.S. PATENT DOCUMENTS

| | | | | |
|---|---|---|---|---|
| 4,884,573 A | * | 12/1989 | Wijay et al. ................ | 128/344 |
| 5,059,178 A | * | 10/1991 | Ya .............................. | 604/101 |
| 5,250,034 A | * | 10/1993 | Appling et al. ............. | 604/164 |
| 5,533,968 A | * | 7/1996 | Muni et al. .................... | 604/96 |
| 5,554,118 A | * | 9/1996 | Jang ............................ | 604/96 |
| 5,700,251 A | * | 12/1997 | Miyauchi et al. ........... | 604/264 |
| 6,277,139 B1 | * | 8/2001 | Levinson et al. ........... | 606/200 |

* cited by examiner

*Primary Examiner*—Thomas Denion
*Assistant Examiner*—Binh Tran
(74) *Attorney, Agent, or Firm*—Oblon, Spivak, McClelland, Maier & Neustadt, P.C.

(57) ABSTRACT

A double lumen-type catheter design which prevents damage to a child catheter and loosening of a stud valve of the double lumen-type catheter. A child catheter is housed inside a parent catheter so that it can freely slide, with the back end of the parent catheter joining with a front end of a Y-type connector with a branching path. The back end of the child catheter extends so that it passes through a back of the Y-type connector toward. A stud valve locks the back end of the child catheter at the back end of the Y-type connector. A cover covers the stud valve at the back end of the Y-type connector and the back end of the child catheter, and is attached so that it can be removed and replaced as needed.

18 Claims, 4 Drawing Sheets

DOUBLE LUMEN-TYPE CATHETER

CROSS-REFERENCE TO RELATED APPLICATIONS

The present document is based on Provisional Application U.S. Serial No. 60/144,247, filed on June 19, 1999, and the entire contents of which are hereby incorporated herein by reference.

BACKGROUND OF THE INVENTION

1. Field of the Invention

The present invention pertains to a double lumen-type catheter including a child catheter and a parent catheter, and pertains more particularly to a double lumen-type catheter with which it is possible to prevent the back end of the child catheter, which extends back through a Y-type connector, from bending and to prevent loosening of a stud valve that is used to lock the child catheter.

2. Discussion of the Background

Double lumen-type catheters generally include a child catheter and a parent catheter that are positioned concentric with one another. A Y-shaped connector is provided at the back end of certain of such types of catheters, with the back end of the parent catheter joining the front end of the Y-type connector. The back end of the child catheter is pushed through the Y-type connector so that it extends out from the back of the Y-type connector, and the child catheter is positioned inside the parent catheter so that it can slide as needed. A stud valve is placed at the back end of the Y-type connector. The back end of the child catheter is locked by the stud valve so that it cannot slide.

However, there is a problem with such background double lumen-type catheters in that bending action is applied and local stress readily accumulates at the back end of the child catheter near the aforementioned stud valve. As a result, the catheter can be quickly and easily damaged by the concentration of the stress that builds up with repeated bending actions. Moreover, if the catheter is improperly handled and the stud valve becomes loose and the child catheter moves, there is a chance that treatment will have to be discontinued or that a medical accident will occur.

OBJECT OF THE INVENTION

One object of the present invention is to provide a novel double lumen-type catheter in which damage to the child catheter and loosening of the stud valve in the aforementioned background double lumen-type catheter can be prevented.

SUMMARY OF THE INVENTION

The present invention accomplishes the aforementioned and other objects by providing a novel double lumen-type catheter in which a child catheter is housed so that it can freely slide inside a parent catheter, with the back end of the parent catheter joining with the front end of a Y-type connector having a branching path. The back end of the child catheter extends so that it passes through the Y-type connector toward the back, and a stud valve that locks the back end of the child catheter is provided at the back end of the Y-type connector. The novel double lumen-type catheter further includes a cover part, which can be removed and replaced as needed, covering the stud valve at the back end of the aforementioned Y-type connector and the back end of the child catheter.

Since the cover part that covers the stud valve and the back end of the child catheter can be removed and replaced as needed, a bending force is not repeatedly applied to the back end of the child catheter, and therefore wearing of the child catheter can be prevented, and loosening of the stud valve can be prevented.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1A:
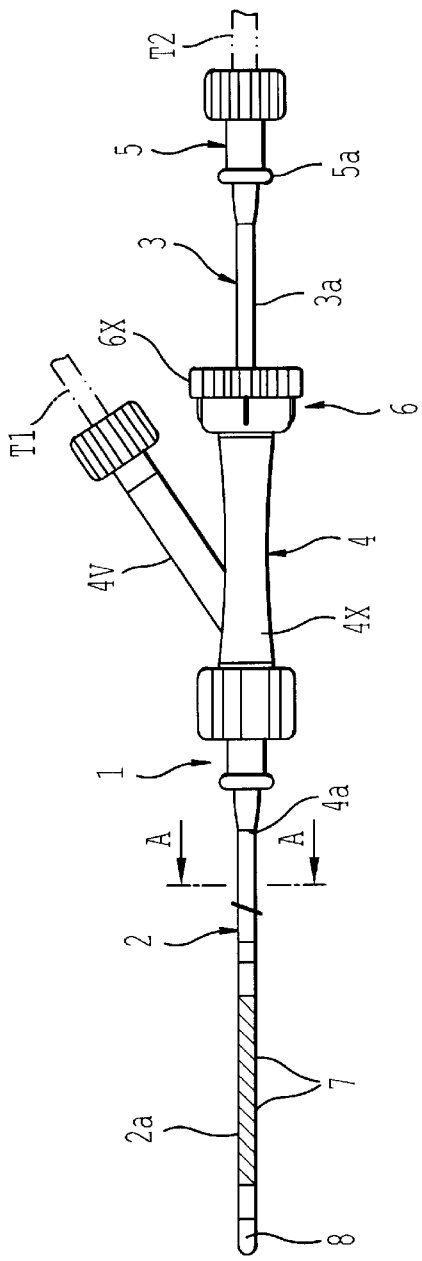
FIG. 1(a) is a front view of a catheter for hemodialysis as an example of the double lumen-type catheter of the present invention.

The structure of the present invention will be described in detail while referring to the attached figures in which like reference numerals designate identical or corresponding parts throughout the several views.

FIG. 1 shows a catheter 1 for hemodialysis, which is one example of the double lumen-type catheter of the present invention. The catheter 1 has a coaxial double-layer structure such as shown in FIG. 2 of a flexible parent catheter 2 and a child catheter 3 inside of the parent catheter 2 to form an interlayer passage 20 therebetween. The child catheter 3 extends back farther than the parent catheter 2, and its head joins with the head of the parent catheter 2 at the head tip 8. The child catheter 3 can slide in the lengthwise direction. The head tip 8 is fastened to the part where the heads of the parent catheter 2 and child catheter 3 join one another. Only the head of the child catheter 3 is open, and the head of the parent catheter 2 is closed.

The back end of the parent catheter 2 is connected to the front end 4a of a Y-type connector 4, which may be made from hard plastic, etc. The Y-type connector 4 includes a connector body 4X, which is a tube that extends straight from the front end 4a of the Y-type connector 4, and a branch 4Y, which is a tube that branches back from a point of the connector body 4X. An extension tube T1 which collects blood can be connected to the branch 4Y. The branch 4Y communicates with the interlayer passage 20 between the child catheter 3 and the parent catheter 2. On the other hand, the Y-type connector 4 and the child catheter 3 are constructed so that the child catheter 3 passes through the back end of the connector body 4X, and such that the back end 3a of the child catheter 3 extends back through the connector body 4X. A extension tube T2 can be connected to a connecting part 5 fastened to the back end 3a of the child catheter 3. A brim part 5a is formed around the outside periphery in the center of the connecting part 5.

Figure 3A:
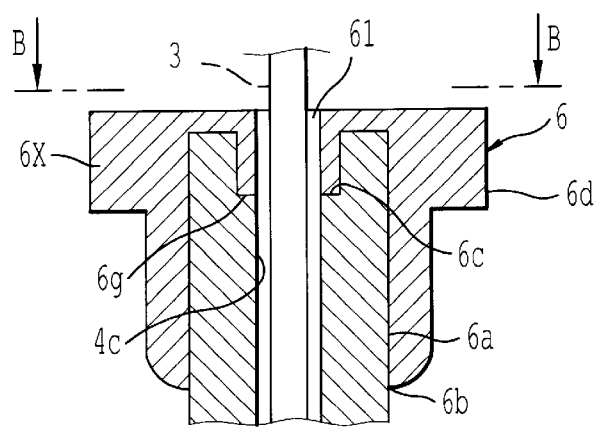
FIG. 3(a) is an enlarged cross-section of a stud valve of FIG. 1.
Figure 3B:
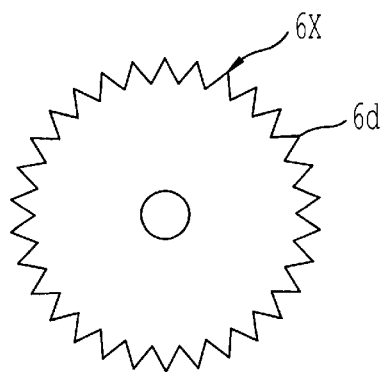
FIG. 3(b) is a view at B—B in FIG. 3(a)

A stud valve 6, which can prevent sliding of the child catheter 3 in the lengthwise direction, and which thus locks the child catheter 3 in place, is placed at the back end of the connector body 4X. As shown in further detail in FIG. 3, the stud valve 6 has a female screw part 6b, which engages with (1) a male screw part 6a which is formed in the outside peripheral face of the back end of the connector body 4X, at its inside peripheral surface, and (2) a knob 6X, which has annular protrusions 6c lined up on the inner periphery side from female screw 6b. Irregularities for stopping sliding are formed on the outer peripheral surface 6d of the knob 6X.

The inner peripheral passage at the back end of the connector body 4X is formed in a large diameter part 6f of the stud valve 6, and a rubber ring 6g fits into the large diameter part 6f. The protrusions 6c push the rubber ring 6g when the knob 6X is turned and tightened. As a result, the back end 3a of the child catheter 3 inside of the inner peripheral passage 4c of the connector body 4X is locked by the rubber ring 6g that has been deformed by being spread out. As a result, sliding of the child catheter 3 is prevented.

Figure 4:
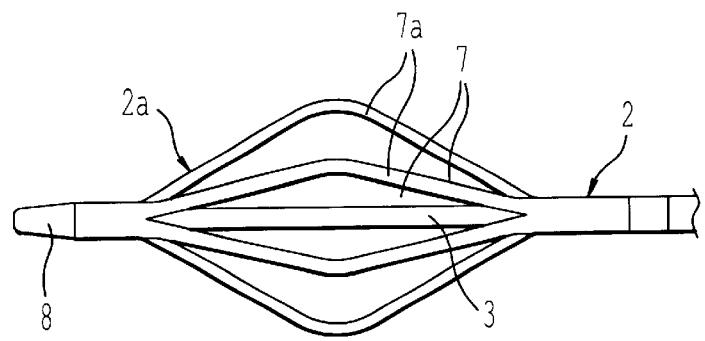
FIG. 4 is an enlarged front view of main parts showing a head of the catheter in FIG. 1 spread open into a basket.
Figure 5:
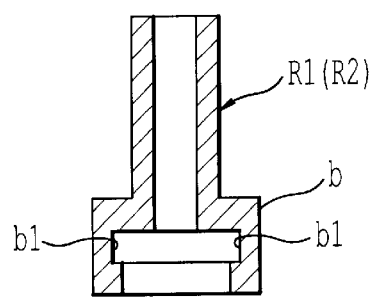
FIG. 5 is a view of two halves of the cover part seen from C—C in FIG. 1(b)

As shown in FIG. 4, a plurality of straight slits 7 are made parallel to the lengthwise direction of head 2A in the parent catheter 2 body. A plurality of strips 7a are thereby formed between the slits 7.

With the aforementioned structure, the child catheter 3 is used to return blood that has been purified during dialysis, and the parent catheter 2 is used to collect blood from inside the body for dialysis. The connecting part 5 becomes a part that operates the catheter 1, and when the connecting part 5 is pulled back, the child catheter 3 moves to the back end of the catheter 1, the head tip 8 is drawn back, and the head 2A of the parent catheter spreads open into a basket shape, as shown in FIG. 4. The open slits 7 then become the outlet for blood from the body. When the connecting part 5 returns to its original position, head 2A closes up into a tube, as shown in FIG. 1(a).

Figure 1B:
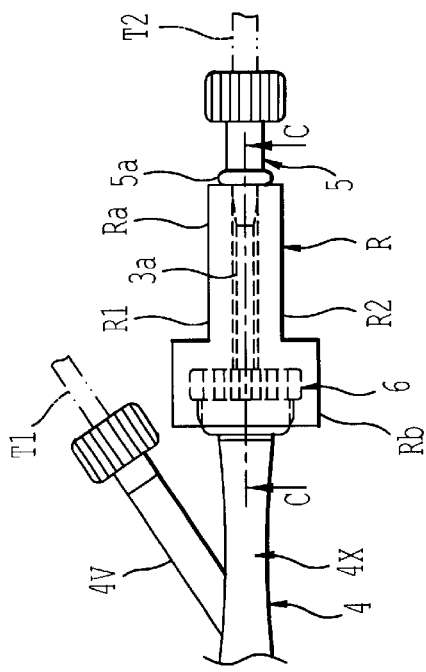
FIG. 1(b) is a front view of main parts of the catheter in FIG. 1(a) showing a cover part attached when the catheter is in use.
Figure 2:
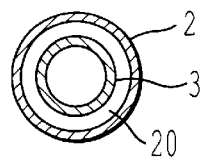
FIG. 2 is an enlarged cross-section of FIG. 1(a) at A—A.

A cover part R, which covers the stud valve 6 at the back end of the Y-type connector 4 and which covers the back end 3a of the child catheter 3, is attached to the catheter 1 as shown in FIG. 1(b), with the head 2A of the parent catheter spread open and the child catheter 3 locked by the stud valve 6. The cover part R, which includes a cylindrical small-diameter part Ra that covers the back end 3a of the child catheter 3 and a cylindrical large-diameter part Rb that completely covers the knob 6X of the stud valve 6, may be divided in two halves R1 and R2, to the left and right of a center axis. The cover part R can be removed and replaced as needed, between the brim 5a of the connecting part 5 and the stud valve 6. The inner peripheral surface of the large-diameter part Rb forms a somewhat elliptic shape, with both ends b of the inner peripheral surface of the large-diameter part Rb of half R1 (R2) becoming the minor axis-side of the ellipse. Therefore, the outer peripheral surface of the knob 6X is engaged, fitted, and fixed so that it slightly cuts into both ends of the inner peripheral surface An agent that cannot be penetrated by X-rays may also be mixed or applied at the heads of the parent catheter 2 and the child catheter 3 so that observation by X-rays is possible during treatment. The head tip 8 at the connecting parts at the heads of the parent catheter 2 and the child catheter 3 is preferably made of a soft material, and catheter 1 can therefore be inserted into a blood vessel without damaging the vessel.

Figure 6:
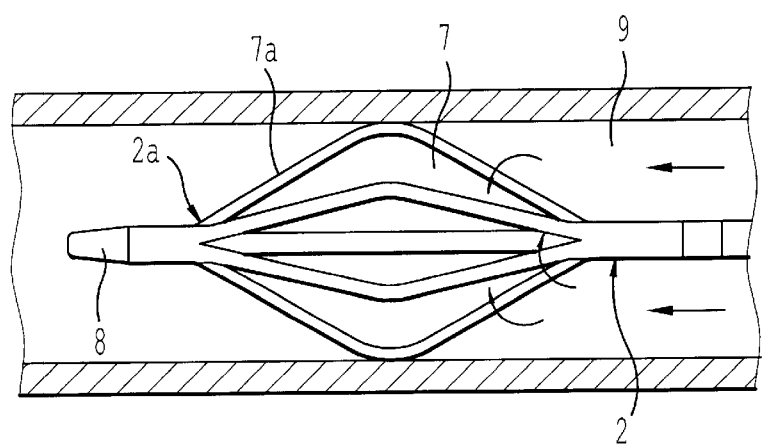
FIG. 6 is an enlarged front view showing the circulation of blood at the head of the catheter of FIG. 1 when it is spread open like a basket inside a blood vessel.

The catheter 1 of the present invention may be used by inserting the head 2A into a blood vessel 9, as shown in FIG. 6. In that operation, as previously mentioned above, the stud valve 6 at the back end of the Y-type connector and the back end 3a of the child catheter 3 are covered by the cover part R, which can be removed and replaced as needed, and therefore, a bending force is not applied to the back end 3a of the child catheter 3, and it is difficult to bend the catheter, and the patient cannot touch and loosen the stud valve 6 by mistake. Further, the cover part R protects the head 2A when the head 2A is open in the basket to prevent kinking and maintain the nominal opening of the basket. Moreover, even if the knob 6X is turned with cover part R and loosened, the brim 5a of the connecting part 5 prevents the child catheter 3 from returning by hitting the small-diameter part Ra of the cover part R, and as a result the head 2A of the parent catheter 2 can usually be kept spread open.

For the present invention, it is possible to use a conventional flexible material that is normally used in catheters to make the parent catheter 2 and the child catheter 3. For instance, polyolefins (such as polyethylene, polypropylene, ethylene-polypropylene copolymer), polyvinyl chloride, polyamide, polyurethane, polyester, fluorine resin (such as polytetrafluoroethylene (PTFE), tetrafluoroethylene hexafluoropropylene copolymer (FEP)), silicone rubber, etc., can be used. Of these, fluorine resin, polyester, and polyurethane are particularly preferred.

Moreover, it is preferred that the outer peripheral surface and the inner peripheral surface of the parent catheter 2 and the child catheter 3 are coated with a biocompatible substance, particularly an anticoagulating substance. Examples of anticoagulants are heparin, urokinase, etc.

The length of each slit 7 may be approximately 2 to 3 cm, and there should preferably be an average of 6 to 10 slits made uniformly around the periphery of the parent catheter 2.

Any conventional material can be used as the material of the cover part R as long as the material will protect the back end 3a of the child catheter 3 and the knob 6X. For instance, hard plastics, etc., are preferred.

Irregularities that engage with the irregularities which are to prevent the knob 6X from slipping can also be formed in the inner surface of the cover part R (inner peripheral surface of large diameter part Rb).

Figure 7:
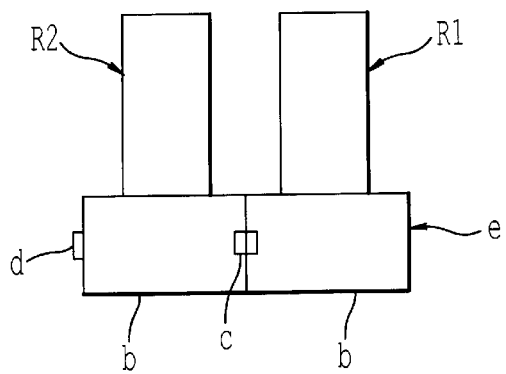
FIG. 7 is a front view showing a view of the cover part when it is open.

Moreover, the structure can also be used whereby one end of both large-diameter parts Rb of halves R1 and R2, where the inner peripheral surface of the large-diameter parts Rb of cover part R is cylindrical, may be joined by a hinge c as shown in FIG. 7, so that the two halves R1 and R2 can be opened and closed, and a concave irregularity d for engagement and a convex irregularity e for engagement are made in the opposite ends and engage when the aforementioned ends are closed. The cover part R is not limited to the aforementioned embodiment as long as it has a structure that can be removed and replaced as needed and can cover the back end 3a of the child catheter 3 and the knob 6X of the stud valve 6.

Figure 8:
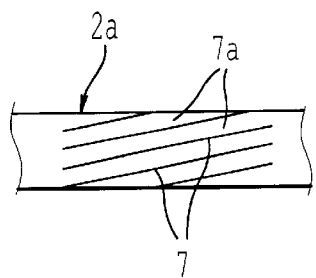
FIG. 8 is an enlarged front view of certain parts in another example of a double lumen-type catheter of the present invention.

Each slit 7 is made in the lengthwise direction in the head 2A of the parent catheter 2 in the aforementioned embodiment, but as shown in FIG. 8, it is also possible to make these slits 7 slanted in the lengthwise direction.

Figure 9A:
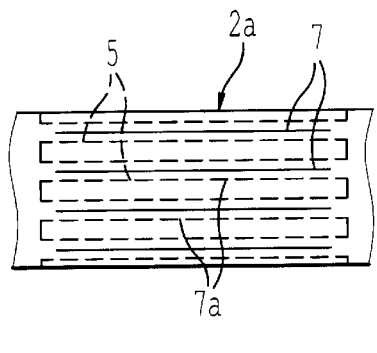
FIGS. 9(a) and (b) are enlarged front views of certain parts of yet other examples of a double lumen-type catheter of the present invention.
Figure 9B:
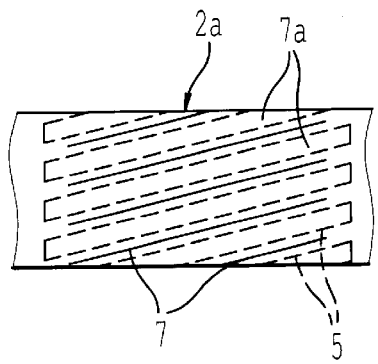

Moreover, as shown in FIGS. 9(a) and 9(b), a reinforcing material S made from a material with a modulus of elasticity (Young's modulus) greater than that of the base material of the parent catheter 2 can be placed on strips 7a. Each reinforcing material S can be extended along slit 7a somewhat past both ends of slit 7a. The reinforcing material S is not necessarily buried within the strip 7a of the parent catheter 2, and it can also be glued to the outer peripheral surface or the inner peripheral surface of the parent catheter 2. The strips 7a can therefore easily spread open without being crushed by blood vessel walls.

The reinforcing material S should be a material with a higher modulus of elasticity (Young's modulus) than the base material of the parent catheter 2, and plastics, metal strips, wires, etc., can be used preferably. The plastic can be polyimide aromatic polyamide, etc., and the metal can be stainless steel, etc.

The present invention has been described in the aforementioned embodiment as a double lumen-type catheter for hemodialysis with which blood is taken outside the body through the slits 7 with head 2A of the parent catheter 2 spreading open into a basket and in which blood is returned to the body through the head of the child catheter 3. However, the present invention is not limited to the aforementioned description, and the present invention is applicable to any embodiment in which a double lumen-type catheter has a back end of a child catheter that can freely slide and extend behind a connector, such as a Y-type connector, connected to a parent catheter, and in which the back end of the child catheter is locked by a valve, such as a stud valve, at the back end of the Y-type connector.

As previously described, the present invention in a preferred embodiment is a double lumen-type catheter with a stud valve 6 that locks the back end of a freely sliding child catheter 3 at the back end of the Y-type connector 4, and where there is a cover part R covering the stud valve 6 at the back end of the Y-type connector and the back end of the child catheter 3 that can be removed and replaced as needed. As a result, damage due to bending of the child catheter 3 and loosening of the stud valve 6 can be prevented.

Obviously, numerous additional modifications and variations of the present invention are possible in light of the above teachings. It is therefore to be understood that within the scope of the appended claims, the present invention may be practiced otherwise than as specifically described herein.

What is claimed is:

1. A double lumen cathode comprising:
   a) a parent catheter;
   b) a child catheter housed in said parent catheter to freely slide within said parent catheter;
   c) a Y-shape connector configured to receive a back end of said parent catheter and said child catheter, the back end of said child catheter extending through a back of said Y-shape connector;
   d) a stud valve positioned at the back of said Y-shape connector and configured to receive the back end of said child catheter to lock the back end of said child catheter; and
   e) a cover configured to be removable and replaceable and configured to cover said stud valve,
   wherein a tip portion of said parent catheter and a tip portion of said child catheter are joined together.
2. A double lumen catheter according to claim 1 wherein said cover comprises
   i) a first half portion and
   ii) a second half portion.
3. A double lumen catheter according to claim 1 wherein:
   (a) said stud valve comprises a knob including a plurality of first irregularities and
   (b) said cover includes a plurality of second irregularities configured to engage with said first irregularities of said knob.
4. double lumen catheter according to claim 2 wherein:
   (a) said stud valve comprises a knob including a plurality of first irregularities and
   (b) said cover part includes a plurality of second irregularities configured to engage with said first irregularities of said knob.
5. A double lumen catheter according to claim 1 wherein:
   (a) said parent catheter comprises a plurality of lengthwise slits to form a plurality of lengthwise strips between respective of said plurality of slits and
   (b) wherein movement of said child catheter causes said plurality of strips to spread open and come together.
6. A double lumen catheter according to claim 5 wherein said plurality of strips are slanted in a lengthwise direction.
7. A double lumen catheter according to claim 6 wherein said parent catheter further comprises a reinforcing material placed on said plurality of strips.
8. A double lumen cathode comprising:
   a) parent catheter means;
   b) child catheter means housed in said parent catheter means for freely sliding within said parent catheter means;
   c) connecting means for receiving a back end of said parent catheter means and said child catheter means, the back end of said child catheter means extending through a back of said connector means;
   d) locking means positioned at the back of said connector means for receiving the back end of said child catheter means and for locking the back end of said child catheter means; and
   e) cover means for covering said locking means,
   (f) said parent catheter means comprises means for forming a plurality of lengthwise strips and
   (g) movement of said child catheter means causes said plurality of strips to spread open and come together.
9. A double lumen catheter according to claim 8 wherein said parent catheter means further comprises reinforcing material placed on said plurality of strips.
10. A double lumen cathode comprising:
    a) a parent catheter;
    b) a child catheter housed in said parent catheter to freely slide within said parent catheter;
    c) a Y-shape connector configured to receive a back end of said parent catheter and said child catheter, the back end of said child catheter extending through a back of said Y-shape connector;
    d) a stud valve positioned at the back of said Y-shape connector and configured to receive the back end of said child catheter to lock the back end of said child catheter; and
    e) a cover configured to be removable and replaceable and configured to cover said stud valve,
    (f) said stud valve comprises a knob including a plurality of first irregularities and
    (g) said cover includes a plurality of second irregularities configured to engage with said first irregularities of said knob.

11. A double lumen catheter according to claim 10 wherein said cover comprises
   i) a first half portion and
   ii) a second half portion.

12. A double lumen catheter according to claim 10 wherein a tip portion of said parent catheter and a tip portion of said child catheter are joined together.

13. A double lumen catheter according to claim 12 wherein:
   (a) said parent catheter comprises a plurality of lengthwise slits to form a plurality of lengthwise strips between respective of said plurality of slits and
   (b) wherein movement of said child catheter causes said plurality of strips to spread open and come together.

14. A double lumen catheter according to claim 13 wherein said plurality of strips are slanted in a lengthwise direction.

15. A double lumen catheter according to claim 14 wherein said parent catheter further comprises a reinforcing material placed on said plurality of strips.

16. A double lumen cathode comprising:
   a) parent catheter means;
   b) child catheter means housed in said parent catheter means for freely sliding within said parent catheter means;
   c) connector means for receiving a back end of said parent catheter means and said child catheter means, the back end of said child catheter means extending through a back of said connector means;
   d) locking means positioned at the back of said connector means for receiving the back end of said child catheter means and for locking the back end of said child catheter means; and
   e) cover means for covering said locking means,
   f) wherein a tip portion of said parent catheter means and a tip portion of said child catheter means are joined together.

17. A double lumen catheter according to claim 16 wherein:
   g) said parent catheter means comprises means for forming a plurality of lengthwise strips and
   h) movement of said child catheter means causes said plurality of strips to spread open and come together.

18. A double lumen catheter according to claim 17 wherein said parent catheter means further comprises reinforcing material placed on said plurality of strips.

* * * * *

UNITED STATES PATENT AND TRADEMARK OFFICE
CERTIFICATE OF CORRECTION

PATENT NO. : 6,579,261 B1  Page 1 of 1
APPLICATION NO. : 09/608609
DATED : June 17, 2003
INVENTOR(S) : Akira Kawamura It is certified that error appears in the above-identified patent and that said Letters Patent is hereby corrected as shown below:

Column 5, line 48: change "cathode" to --catheter--
Column 6, line 27 claim 8: change "cathode" to --catheter--
Column 6, line 48 claim 10: change "cathode" to --catheter--
Column 7, line 22 claim 16: change "cathode" to --catheter--

Signed and Sealed this

Third Day of August, 2010

David J. Kappos
*Director of the United States Patent and Trademark Office*